US00PP26769P3

(12) United States Plant Patent
Maillard et al.

(10) Patent No.: US PP26,769 P3
(45) Date of Patent: May 31, 2016

(54) NECTARINE TREE NAMED 'CAKEREVE'

(50) Latin Name: ***Prunus persica* (L.) Batsch**
Varietal Denomination: CAKEREVE

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 52 days.

(21) Appl. No.: 13/999,364

(22) Filed: Feb. 18, 2014

(65) Prior Publication Data

US 2015/0237778 P1 Aug. 20, 2015

(51) Int. Cl.
*A01H 5/08* (2006.01)

(52) U.S. Cl.
USPC ..... Plt./188

(58) Field of Classification Search
USPC ..... Plt./188, 187, 189
See application file for complete search history.

(56) References Cited

PUBLICATIONS

Redacted invoice from ASF to SAT1499CAT1 dated Feb. 14, 2014; with English machine translation (3 pages).
Redacted contract between ASF and SAT1499CAT1 dated Feb. 14, 2014; with English machine translation (10 pages).
France plant application for CAKEREVE dated Nov. 27, 2012; with English machine translation (2 pages).
European Community plant application for CAKEREVE No. 2012/2708 dated Nov. 27, 2012; with English machine translation (2 pages).
European Community Official Gazette excerpt for CAKEREVE dated Feb. 15, 2013; in English (12 pages).
Information table for CAKEREVE (Oct. 8, 2013); with partial English machine translation (5 pages).
Information sheet for CAKEREVE dated Jan. 2016; with English machine translation (2 pages).

*Primary Examiner* — Susan McCormick Ewoldt
(74) *Attorney, Agent, or Firm* — Westerman, Hattori, Daniels & Adrian, LLP

(57) ABSTRACT

A new and distinct variety of white flat nectarine tree denominated 'CAKEREVE' has fruits with high eating quality and very long shelf life without alteration before and after harvesting, with a semi-sweet white flesh, with a slightly red pigmentation close to the skin, near the pistil, and an attractive luminous skin with a high percentage of purple red blush on skin surface, on an orange red background.

2 Drawing Sheets

Botanical classification: *Prunus persica* (L.) Batsch.
Variety denomination: 'CAKEREVE'.

BACKGROUND OF THE NEW VARIETY

The present invention relates to a new and distinct variety of white flat nectarine tree, *Prunus persica* (L.) Batsch, which has been given the variety denomination 'CAKEREVE'.

This new tree produces fruits with a long shelf life without alteration both on the tree after growth completion and after harvesting, very good eating quality, semi-clingstone white flesh fruits, slightly greenish, with a very slightly red pigmentation near the epidermis, for fresh market in August in the Pyrénées-Orientales department, France.

ORIGIN OF THE VARIETY

The 'CAKEREVE' white flat nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'CAKEREVE' variety results from a pollinated cross between a white nectarine tree named 'NECTARJEWEL' (U.S. Plant Pat. No. 19,380) which was used as a seed parent and the 'ASFNBF0471' (not patented) white flat nectarine tree which was used as the pollen parent.

'CAKEREVE' was provisionally designated, tested and genetically identified by a genetic profile, under number 03.21 W.39.

The 'CAKEREVE' variety was obtained by hybridizing and propagated by grafting on a 'INRA GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'CAKEREVE' white flat nectarine tree blooms at the end of February or early in March near Elne in the Pyrénées-Orientales department, France. The blooming period is considered medium. However, it was observed that its late date of blooming seems to be highly dependant on climatic conditions.

The first fruit of 'CAKEREVE' ripens generally early to medium season, in the beginning or middle of July. More particularly, it usually ripens between July 1$^{st}$ and July 12$^{th}$. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
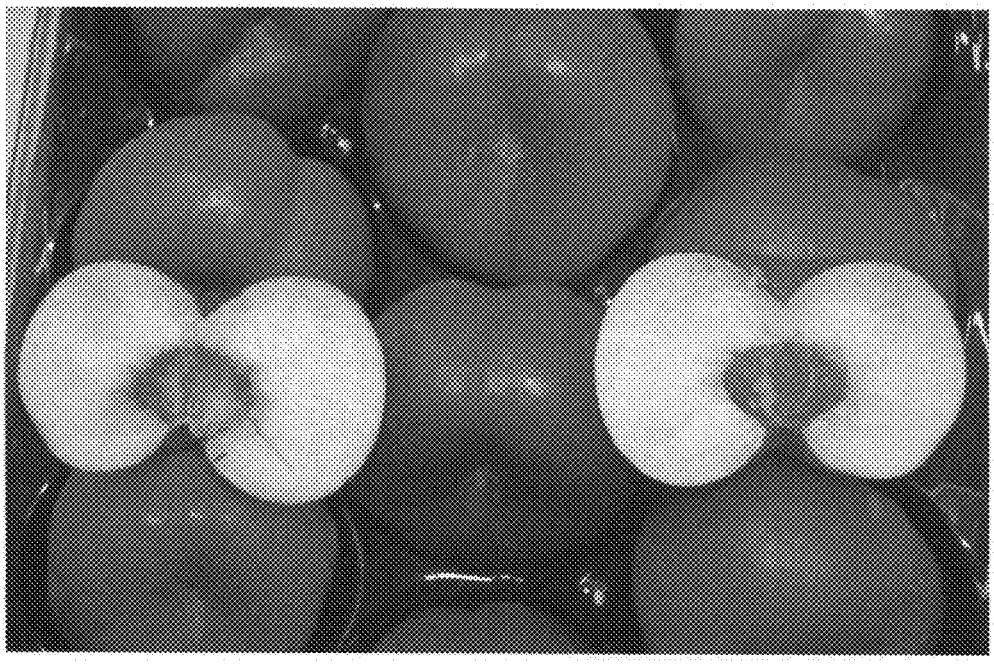
FIG. 1 is a color photograph that shows a close view of typical specimens of the fruit of the new variety 'CAKEREVE' at ripening time, one fruit having been cut in half with the pit being left in one of the halves.
Figure 2:
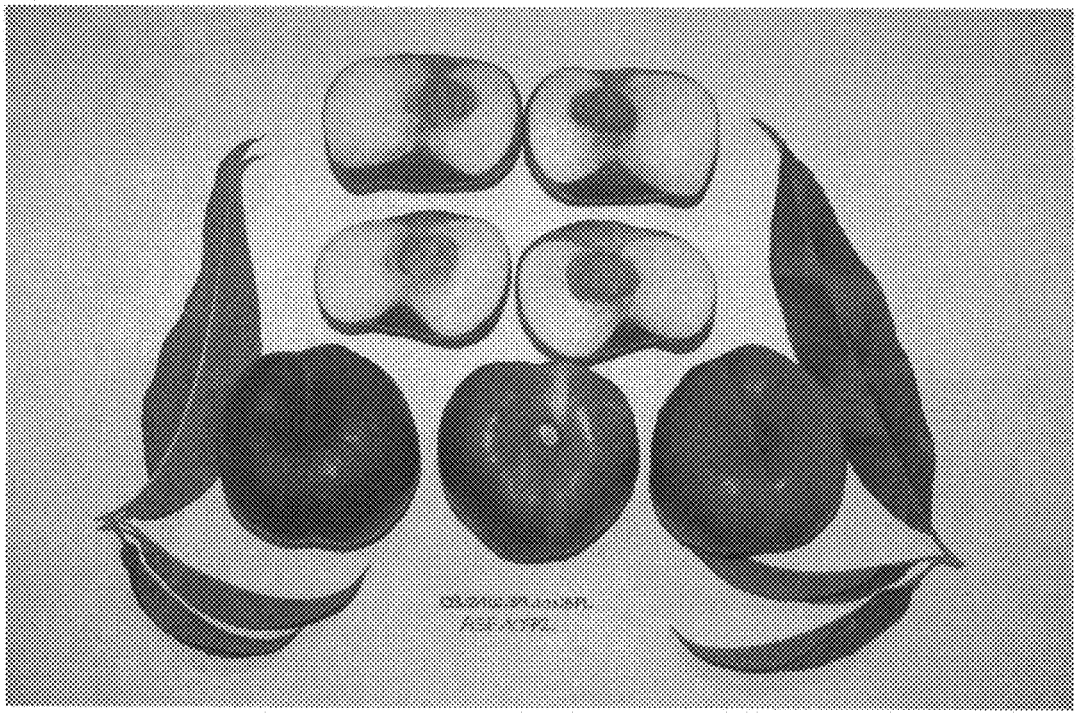
FIG. 2 is a color photograph which shows five typical specimens of the fruit, two of them having been cut in half with the pit being left in one of the halves for depicting leaves, fruit flesh, pit and pit cavity of the new variety
Figure 3:
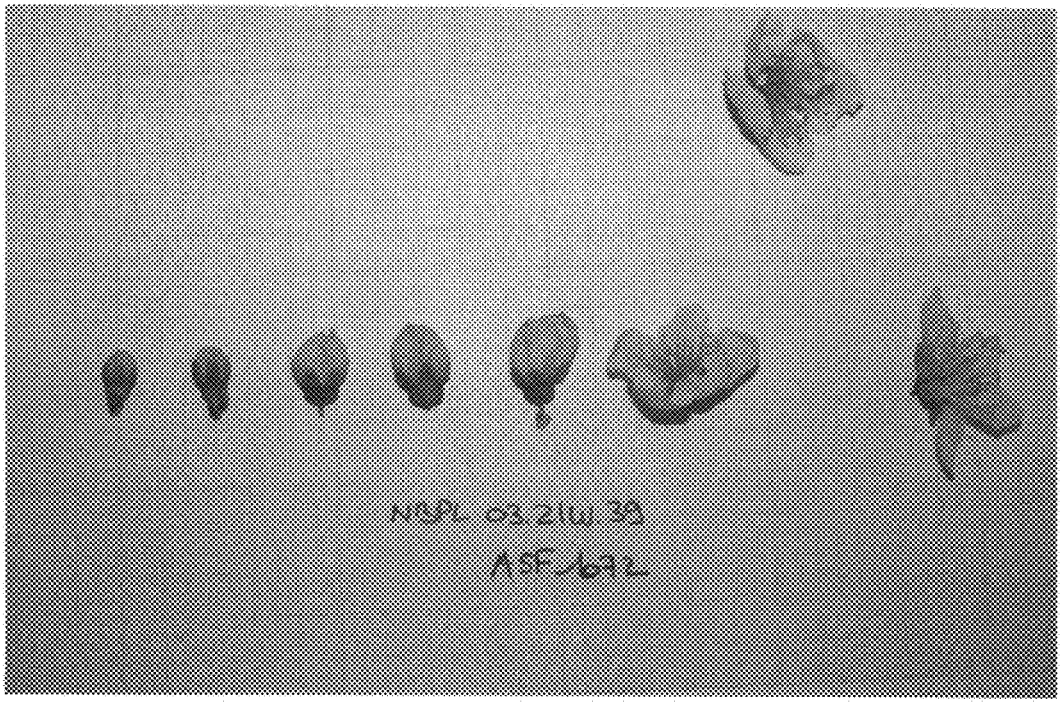
FIG. 3 is a color photograph which depicts the flower buds at different development stages, and the reverse and side view of the flower and the reproductive organs with petals removed, of the new variety.
Figure 4:
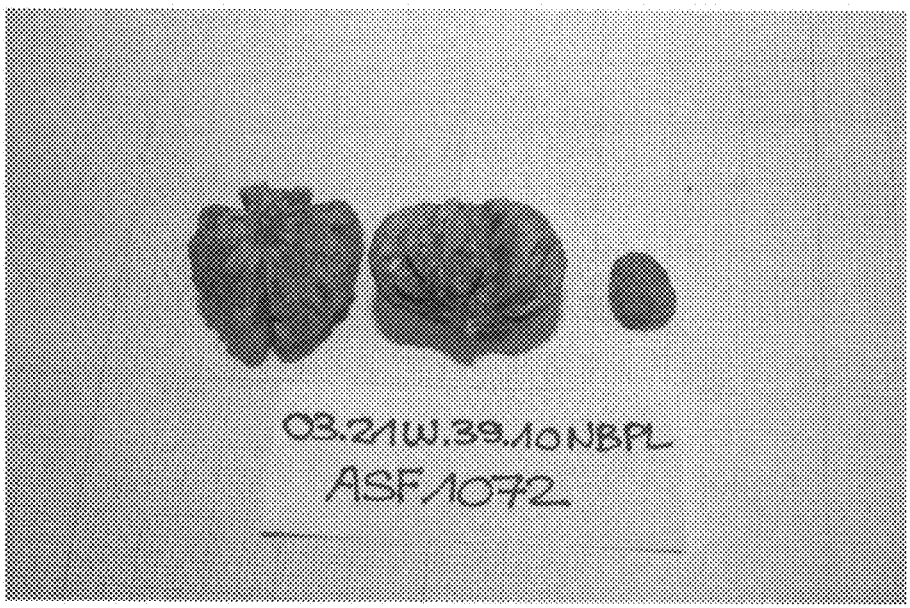
FIG. 4 is a color photograph of the stone of the new variety.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CAKEREVE' is high, due to fruit very long shelf life without alteration after harvesting.

Trees are vigorous and large stature half-standing in a semi-flared to semi-upright out aspect. The anthocyanic coloration of flowering shoot is present excluding brushwood side away from sun. The time of beginning of flowering is considered medium; flowering begins at the end of February or early in March. The type of flower is showy with medium petal size. Petals are medium pink. Leaf glands are present and reniform. The fruit flesh is white, slightly greenish, and generally with a very slightly red pigmentation near the skin, more particularly near the pistils. The fruit skin is very thick, with a luminous purple red blush on an orange red background.

The stone is semi-clingstone and his size is medium. Fruit taste is semi-sweet, very aromatic and with a high level of sugars.

Compared to 'ASFNBF0774' variety (not patented), the fruits of 'CAKEREVE' variety ripen approximately at the same time. The maturity of 'CAKEREVE' variety is considered early to medium. The fruits from 'CAKEREVE' variety are bigger than fruits from 'ASFNBF0774' variety. 'CAKEREVE' fruits show a closed pistil cavity, and without any cork formation. In comparison, 'ASFNBF0774' fruits possess a pistil cavity barely closed, with a little amount of cork, that could lead to a susceptibility to rot.

Compared to 'ASFNBF0471' (not patented) variety, which is the male parent, 'CAKEREVE' variety blooms 4 days earlier and 'CAKEREVE' fruits ripen 15 days earlier. Moreover, the fruits of 'ASFNBF0471' variety possess a pistil cavity barely closed, with a little amount of cork, that could lead to a susceptibility to rot. After the harvest, the lifespan of 'ASFNBF0471' fruits is medium whereas the 'CAKEREVE' fruits have a long life both on the trees and after the harvest.

Compared to 'NECTARJEWEL' (U.S. Plant Pat. No. 19,380) variety, used as the female parent, the fruits which are produced by 'CAKEREVE' variety are flat, whereas 'NECTARJEWEL' fruits are round-shaped. Furthermore, 'CAKEREVE' variety ripens approximately 1 month earlier than 'NECTARJEWKL' variety.

DETAILED DESCRIPTION

Referring more specifically to the pomological details of this new and distinct variety of white flat nectarine tree, the following was observed on trees in their third growing season (second year of production) under the ecological conditions prevailing at the orchards located near the town of Elne, Pyrénées-Orientales departement, France. All observations have been done on rootstock cultivars. Used rootstocks were 'INRA GF677' (non-patented) trees. All major color code designations are by reference to The R.H.S. Colour Chart (Fourth Edition) provided by The Royal Horticultural Society of Great Britain.

Tree:

*Size.*—Generally. — Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduces to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered strong.

*Productivity.*—Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety. A reduce vegetation, obtained with pruning or green pruning, approximately 1 month or 1 month ½ before harvesting flat fruits, significantly promotes fruit qualities, especially growth, color and firmness. Moreover, contamination risks due to monilia or rot are significantly reduced. 'CAKEREVE' variety is not much sensitive to cracking of pistil cavity, to cork formation into peduncle cavity or to monilia.

*Bearer.*—Very regular. The fruit distribution is considered homogenous on mixed branches and spurs having more than 1 year. Thinning of 2 fruits out of 3 was necessary for the tree valorisation. Thinning was necessary every year during the years of observation.

*Form.*—The 'CAKEREVE' variety has naturally a semi-flared to semi-upright shape.

*Density.*—Considered dense.

*Hardiness.*—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. Traditionally, flat fruits are more sensitive to critical low temperatures and to climatic variations, because of the flower morphology in which the ovule is less protected than in the classical round fruits. Thus, areas not much exposed to frost are recommended for trees growth. However 'CAKEREVE' trees seem to be very resistant to critical frosty weather.

Trunk:

*Diameter.*—Approximately 63 millimeters in diameter when measured at a distance of approximately 30 centimeters above the soil level.

*Bark texture.*—Considered slightly rough, with lenticels.

*Lenticels.*—Numerous lenticels are present. The lenticels range in size from approximately 2.0 to 4.0 millimeters in width, and about 1.5 millimeters in height.

*Lenticel color.*—The outside of lenticels has a silver-grey color (RHS Grey 201 D or RHS Black 202 D), whereas the inside is considered brown (RHS Greyed Orange 166 B).

*Bark coloration.*—The bark has a silver-grey color (RHS Grey 201 C or RHS Black 202 C) slightly darker than the outside of lenticels color.

Branches:

*Size.*—Mature branches and current season shoots are considered medium for the variety.

*Diameter.*—Average as compared to other nectarine varieties. The current season shoots have a diameter from 5.0 to 7.0 millimeters, and mature branches have a diameter from 15.0 to 19.0 millimeters.

*Surface texture.*—Average, wood which is several years old has no furrowed appearance.

*Crotch angles.*—Primary branches are considered variable, but the crotch angles are generally between 60 degrees and 80 degrees from the horizontal axis. This particular characteristic is not considered distinctive of the variety, however.

*Current season shoots.*—Internode length: Generally between 25.0 and 35.0 millimeters. Color of mature branches: Grey brown (RHS Grey Brown 199 A to RHS Grey Brown 199 B).

*Current seasons shoots.*—Color. — The color of new shoot tips is considered yellow-green (RHS Green 144 A to RHS Green 144 C) on lower part of new shoot tips, whereas the upper part is darker and colored in brown-purple more or less deep (RHS Greyed Red 187 A to RHS Greyed Red 187 B or RHS Greyed Red 182 A to RHS Greyed Red 182 C), depending on the level on the tip and the sunlight exposure.

Leaves:

*Size.*—Considered medium to large for the species. The ratio leaf length/leaf width is 3.76.

*Leaf length.*—Approximately 124.0 to 160.0 millimeters with leaf petiole. The medium length is about 149.1 millimeters.

*Leaf width.*—Approximately 34.0 to 49.0 millimeters. The medium width is 39.6 millimeters.

*Leaf base shape.*—Lanceolate, lance-shaped.

*Leaf form.*—Lanceolate.

*Leaf tip form.*—Short, pointed and acuminate.

*Leaf color.*—Upper leaf surface. — Dark Green (RHS Green Group 137 A). Lower surface. — A lighter green (RHS Green Group 137 B to RHS Green Group 137 C) than the upper leaf surface color.

*Leaf texture.*—Both upper and lower leaf surfaces are considered smooth and glabrous.

*Leaf venation.*—Pinnately veined.

*Mid-vein.*—Color. — Light green, almost cream white (RHS Yellow Green 145D). The color may evolve with maturity.

*Leaf margins.*—Slightly undulating.

*Form.*—Leaf margins are considered slightly dentate.

*Uniformity.*—Leaves are isolated or grouped by 2 or 3. In this last case, one leaf of normal size is found with one or two smaller leaves (at least 50% smaller).

*Leaf petioles.*—Size. — Considered medium. Length. —About 11.0 to about 18.0 millimeters. Diameter. — About 1.5 millimeters.

*Petioles color.*—Upper petiole surface. — Light green (RHS Yellow Green 144 A). Lower surface. — Light green (RHS Yellow Green 145 A).

*Leaf glands.*—Size. — Considered medium to large. Their length is about 2.0 millimeters and their width is about 1.0 millimeter. Number. — Generally 2 glands per leaf. Type. — Reniform. Margins. — Smooth and regular. Color. — On young leaves, leaf glands color is considered a light green (RHS Green 145 B). On older leaves, leaf glands color turns to a dark brown (RHS Grey Brown 199 A to RHS Grey Brown 199 B). Margins. — Smooth and regular.

*Leaf stipules.*—Generally. — No leaf stipules were observed. But as seen in the characteristic relative to the leaves uniformity, it is possible to find leaves by groups of 2 or 3, with a normal-size leaf and smaller ones.

Flowers:

*Flower buds.*—Generally. — At pre-floral stage of development, the floral buds are conic in form with a round tip. Their form is evolving until blooming, with variables dimensions. Just before blooming, floral buds are approximately 14.0 millimeters wide and approximately 16.0 millimeters long. Color. — This characteristic is dependent upon the proximity to bloom. At pre-floral stage of development, the bottom of the flowers buds, formed by the sepals, is of purple-brown color (RHS Greyed Purple 183 A to RHS Greyed Purple 183 D or RHS Grey Brown Group 199 A). The corolla, formed by the petals, is generally of medium pink color (RHS Red Purple 62 A to RHS Red Purple 62 B). Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins at the end of February or early in March. The first bloom was observed on Feb. 24, 2011.

*Blooming time.*—Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus the full bloom was observed in 2011, from Feb. 24$^{th}$ until Mar. 4$^{th}$, from Mar. 9$^{th}$ until Mar. 20$^{th}$ in 2012 and the from Feb. 17 until Mar. 4, 2013.

*Duration of bloom.*—Approximately between 7 to 15 days. This characteristic varies slightly with the prevailing climatic conditions.

*Flower type.*—The variety is considered to have a showy type flower.

*Flower size.*—Considered medium. Flower diameter at full bloom is approximately 28.0 to 38.0 millimeters.

*Bloom quantity.*—Considered abundant, approximately between 30 and 40 flowers per meter, with a high rate of fruit set. The bloom is heterogeneous, and the bloom quantity is more important on the top of the tree.

*Flower bud frequency.*—Generally 2 flower buds appear per node, occasionally 1.

*Petal size.*—Generally. — Considered medium. Length: Generally between 16.0 and 19.0 millimeters. The medium length is 18.25 millimeters. Width: Generally between 15.0 and 17.0 millimeters. The medium width is about 16.12 millimeters.

*Petal form.*—Round-shaped.

*Petal count.*—Generally 5.

*Petal texture.*—Smooth and soft.

*Petal color.*—Both surfaces of the petal are colored with a medium Pink (RHS Red Purple 65 B to RHS Red Purple 65 D) when young, becoming slightly darker until the end of blooming.

*Fragrance.*—Sweet.

*Petal claw.*—Form. — The claw is considered to have a conic form, slightly round at the top. Length. — About 6.0 millimeters. Width. — About 4.0 millimeter at the base.

*Petal margins.*—Generally considered wavy, sinuate.

*Petal apex.*—Generally. — The petal apices are generally wide dome-shaped, very slightly undulating.

*Flower pedicel.*—Length. — Considered medium to large and having an average length of approximately 4.0 millimeters. Diameter. — Considered average, approximately 1.0 to 2.0 millimeters. Color. — Light green (RHS Yellow Green 144 B to RHS Yellow Green 144 C).

*Calyx.*—Internal surface texture. — Smooth and glabrous. Color. — The inner surface of the calyx is green yellow (RHS Yellow Group 13 A to RHS Yellow Group 13 B or RHS Yellow Green 150 A to RHS Yellow Green 150 B). The outer surface of the calyx is considered of purple-brown (RHS Greyed Purple 183 A to RHS Greyed Purple 183 D) color.

*Sepals.*—Surface texture. — The outer surface has a short, fine pubescent texture. Size. — Medium to large. Form. — Oval. Color. — Both sides of sepals are colored with a matt Red (RHS Greyed Purple 183 A to RHS Greyed Purple 183 D or RHS Grey brown Group 199 A).

*Average number of stamens per flower.*—Approximately 43 to 47 stamens per flower.

*Anthers.*—Generally. — medium in length. Color. — At an early stage of maturity, anthers are colored with an orange yellow (RHS Yellow Orange 16 A to RHS Yellow Orange 16 B) or an orange red to red color (RHS Greyed Red Group 178 A). The color may evolve with maturity to turn in a yellow color.

*Pollen production.*—Pollen is abundant, and has a orange yellow color (Approximately RHS Yellow Orange 17 B to RHS Yellow Orange 17 C) which may evolve with maturity. The present variety is considered auto-fertile (self-pollinating).

*Pollination.*—Pollen is abundant and autofertil, good compatibility in controlled hybridization.

*Filaments.*—Size. — Medium length, between 7.0 and 16.0 millimeters in length. Filaments length is generally the same or slightly higher than the pistil's length. Color: Considered pale pink (RHS Red Purple 62 C to RHS Red Purple 62 D) or darker pink (RHS Red Purple 73 A to RHS Red Purple 73 B). The color becomes darker during the blooming.

*Pistil.*—Number. — Usually 1, sometimes more than one. Generally. — Average in size. Length. — Approximately 17.0 to 19.0 millimeters including the ovary. Generally equal to stamen length, if not slightly smaller. Color. — Considered a very pale green (RHS Yellow Green Group 150 D or RHS RHS Yellow Green Group 151 D). The color evolves during the blooming. Surface texture. — Glabrous Ovary. — No pubescence.

Fruit:

*Maturity when described.*—Very firm in ripe conditions (shipping ripe).

*Date of first picking.*—Jul. 25, 2010.

*Date of last picking.*—The date of harvest varies slightly with the prevailing climatic conditions. The 'CAKEREVE' variety has an early to medium date of picking, and a grouped maturity. The maturity is grouped within 12 days and the harvest is generally performed in two runs. Last known picking times carry on Jul. 25 to Aug. 2, 2010, then on Jul. 1 to Jul. 7, 2011, then on Jul. 12 to Jul. 24, 2012, then on July 8 to Jul. 18, 2013.

*Size.*—Generally. — Homogeneous in size. Considered medium to large.

*Average cheek diameter.*—Approximately 71.0 to 77.0 millimeters.

*Average axial diameter.*—Approximately 44.0 to 49.0 millimeters.

*Typical weight.*—Generally about 120.0 grams. This characteristic is high dependent upon the prevailing cultural practices, and therefore is not particularly distinctive of the variety.

*Fruit form.*—Generally. — Round and flattened, generally with few bump. The fruit is generally uniform in symmetry, viewed from the suture's plane.

*Suture.*—Fruit suture: Wide-mouthed and slightly marked, extending from the base to the apex. No apparent callousing or stitching exists along the suture line. Not pointed. Color. — The suture has generally a similar color to the whole fruit color, a luminous purple red (RHS Greyed Purple 187 A or RHS Greyed Purple 187 B).

*Ventral surface.*—Form. — Smooth.
*Apex.*—slightly depressed.
*Base.*—Semi-flared, shallow.
*Stem cavity.*—Average depth of the stem cavity is about 8.0 to 9.0 millimeters. Average width is about 13.0 to 16.0 millimeters.
*Fruit skin.*—Thickness. — Considered thick and strong, and the adherence of skin to flesh is strong to medium, depending on the fruit maturity. Texture. — Smooth. Taste. — Semi-sweet, sugary. Tendency to crack. — None observed.
*Color.*—Blush color. — This blush color is a luminous purple red (RHS Greyed Purple 187 A or RHS Greyed Purple 187 B).). The purple red blush covers 80% to 90% of the fruit skin surface on an orange red background (RHS Orange Red N34 A) on approximately 10% to 20% of the fruit skin surface. The percentage of the blush on the fruit skin surface can vary, and is generally dependant upon the prevailing conditions under which the fruit was grown. Ground color. — The ground color covers approximately 10% to 20%of the fruit skin surface, and is considered orange red (RHS Orange Red N34 A).
*Fruit stem.*—Medium in length, approximately 7.0 to 9.0 millimeters.
*Diameter.*—Approximately 5.0 millimeters.
*Color.*—Pale green (RHS Yellow Green 145 A to RHS Yellow Green 145 B).
*Flesh.*—Ripens. — Very homogenously, slowly. The flesh has a long shelf life. Texture. — Very firm, very dense, crunchy, melting, juicy at harvest maturity stage. Fibers. — Not fibrous. Aroma. — Very pronounced. Eating quality. — Considered very good, aromatic. Flavor. — Considered semi-sweet. The Brix is generally superior to 12 and acidity comprised between 6 and 9 meq/100 ml. Juice. — Juicy to Very juicy at complete maturity. Brix. — Generally 12.0 to 13.0 degrees. This characteristic varies slightly with the number of fruit per tree; prevailing cultural practices; and the surrounding climatic conditions. Flesh color. — White flesh (RHS Green White 155 C to RHS Green White 155 D), very slightly greenish, usually with a slightly red pigmentation close to the skin, near the pistil.

Stone:
*Type.*—Semi-Clingstone, more or less semi-adherent depending on the fruit maturity.
*Size.*—Considered medium for the variety. The stone size varies significantly depending upon the tree vigor, crop load and prevailing growing conditions.
*Length.*—Approximately 23.0 to 25 millimeters.
*Width.*—Approximately 23.0 to 25.0 millimeters.
*Diameter.*—Approximately 15.0 to 17.0 millimeters.
*Form.*—Flattened.
*Base.*—Straight.
*Apex.*—Shape. — The stone apex is flattened.
*Stone cavity.*—Considered medium size, with flattened form and dimensions corresponding to the stone's dimensions.
*Stone surface.*—Surface texture. — The pit is transversely furrowed on its entire surface. Furrows are deeper and more oblate on lateral sides. Ridges. — The surface texture is generally characterized by more prominent ridges along the ventral edges and at the apical tip.
*Ventral edge.*—Width. — approximately 2.3 millimeters at mid-suture.
*Dorsal edge.*—Shape. — Grooved.
*Stone color.*—The color of the dry stone is generally considered light orange brown (RHS Greyed Orange 165 B or RHS Greyed Orange 165 C).
*Tendency to split.*—Splitting is very low or absent, depending on climatic conditions between blooming period and stone hardening.
*Kernel.*—Size. — The kernel is considered medium. Length. — Approximately 10.0 millimeters. Width. — Approximately 8.0 millimeters. Thickness. — Approximately 6.0 millimeters. Form. — Considered flattened and elliptic. Sometimes double. Pellicle. — The pellicle of the kernel has a short pubescence. Color. — The kernel skin is orange-brown colored (RHS Greyed Orange N167 B). The almond, which is the seed of the kernel, is white (RHS White 155 B) and has a bitter tasting. The kernel and its embryo are mature at the time of fruit maturity.

Use: The subject variety 'CAKEREVE' is considered to be a white flat nectarine tree of the early or medium season of maturity, and which produces fruits that are considered firm, attractively colored with a very luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

Keeping quality: Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

Shipping quality: Considered very good. The fruit of the new white flat nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

Resistance to insects and disease: No particular susceptibilities were noted. The present variety is not very sensitive to Monilia or rot. The pistil cavity is completely closed, generally without any cork formation.

Although the new variety of white flat nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of white flat nectarine tree as illustrated and described, characterized by fruits with high eating quality and very long shelf life without alteration before and after harvesting, with a semi-sweet white flesh, with a slightly red pigmentation close to the skin, near the pistil, and an attractive luminous skin with a high percentage of purple red blush on skin surface, on an orange red background.

* * * * *